United States Patent [19]

Chao

[11] 4,016,335
[45] Apr. 5, 1977

[54] UREA-GLYOXAL-FORMALDEHYDE CELLULOSE REACTANT

[75] Inventor: Tsai Hsiang Chao, Somerville, N.J.

[73] Assignee: American Cyanamid Company, Stamford, Conn.

[22] Filed: Feb. 7, 1975

[21] Appl. No.: 548,109

Related U.S. Application Data

[62] Division of Ser. No. 356,685, May 2, 1973, Pat. No. 3,903,033.

[52] U.S. Cl. .................................. 428/526; 8/185; 260/29.4 R; 260/70 R; 260/309.7; 427/381; 427/390 R; 427/390 C; 427/370
[51] Int. Cl.$^2$ .................. B05D 3/12; B05D 3/02
[58] Field of Search ......... 8/185; 260/29.4 R, 70 R, 260/309.7; 427/381, 390, 370; 428/526

[56] References Cited
UNITED STATES PATENTS

| | | | |
|---|---|---|---|
| 2,876,062 | 3/1959 | Torke et al. | 8/185 |
| 3,487,088 | 12/1969 | Remley | 260/309.7 |
| 3,801,546 | 4/1974 | Peterson et al. | 260/69 R |

Primary Examiner—Michael R. Lusignan
Attorney, Agent, or Firm—Robert J. Feltovic; H. G. Jackson

[57] ABSTRACT

A process for preparing stable aqueous solutions of a water-soluble urea-formaldehyde-glyoxal condensation product in which urea, glyoxal and formaldehyde are reacted under very slightly acidic conditions of pH and at a temperature of from 40° to 90° C., further reacted under more acidic conditions of pH and at a temperature of from 40° to 90° C., and then adjusted to very slightly acidic conditions of pH.

6 Claims, No Drawings

UREA-GLYOXAL-FORMALDEHYDE CELLULOSE REACTANT

This is a division of application Ser. No. 356,685 filed May 2, 1973 now U.S. Pat. No. 3,903,033, patented Sept. 2, 1975.

FIELD OF THE INVENTION

This invention relates to a process for the preparation of a cellulose reactant composition to impart durable press properties to cellulosic textile materials.

DESCRIPTION OF THE PRIOR ART 1,3-Dimethylol-4,5-dihydroxy-2-imidazolidinone has the following structural formula:

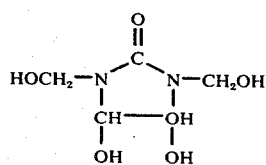

The above imidazolidinone has become a valuable textile finishing agent particularly for use as a crease proofing agent on cellulosic textile materials including blends of such materials with other fibers such as polyamides and polyesters. Although it may be employed as a conventional crease-proofing finish in the manner described in U.S. Pat. No. 2,731,364, its present commercial importance is as a postcure crease-proofing finish of the type employable in the process described in U.S. Pat. No. 2,974,432.

There are various processes for preparing 1,3-dimethylol-4,5-dihydroxy-2-imidazolidinone from urea, glyoxal and formaldehyde. In one, urea and glyoxal are reacted under alkaline conditions to produce 4,5-dihydroxy-2-imidazolidinone, which is then reacted with formaldehyde under neutral or alkaline conditions (see U.S. Pat. Nos. 2,731,472 and 2,764,573). In another process, urea and formaldehyde are reacted under alkaline conditions to produce dimethylol urea which is then reacted with glyoxal under alkaline conditions to form the imidazolidinone. (see Pat. No. 2,876,062). According to U.S. Pat. No. 3,049,446, the product of the first mentioned process, that described in U.S. Pat. Nos. 2,731,472 and 2 764,573, is dark brown and discolors cloth unless the intermediate monourein is purified before it is reacted with formaldehyde. In still another process, urea and glyoxal are reacted at a pH of from 3.8–4.2, followed by reaction with formaldehyde at a pH of 7.0–7.5. (see British Pat. No. 1,032,379).

In the above processes the yield is often low and the products contain large amounts of unreacted formaldehyde and glyoxal. In the case of the process described in U.S. Pat. No. 2,876,062, the product has been found to be unstable as evidence by discoloration of aging. In other processes, urea and formaldhyde are reacted with glyoxal in one step to form the imidazolidinone. (see U.S. Pat. No. 3,487,088).

In the processes of the prior art the end products have a deficiency in that the fabrics treated therewith release high levels of formaldehyde before curing thereby causing pollution and a hazardous condition in the immediate environment of the employees of the finishing company. I have reduced this hazard significantly by using the water-soluble urea-formaldehyde-glyoxal condensation products of my invention.

SUMMARY OF THE INVENTION

The invention is a process for preparing a textile finish composition of an aqueous solution of a water-soluble urea-formaldehyde-glyoxal condensation product and the composition and the use of the composition on textiles to produce a curable finish having a low level of emission of formaldehyde which when cured imparts desirable durable press properties to the textile materials thus treated.

DETAILED DESCRIPTION

The invention provides a process for preparing aqueous solutions of a water-soluble urea-formaldehyde-glyoxal condensation product containing 1,3-dimethylol-4,5-dihydrox-2-imidazolidinone, sometimes referred to as dimethylol monourein or dimethylol dihydroxyethyleneurea, that are characterized by low levels of formaldehyde released by fabrics treated therewith and which are effective as durable press agents for cellulosic textile materials.

The invention provides a three-step process for preparing the water-soluble urea-formaldehyde-glyoxal condensation product which comprises reacting in a first step relative amounts of 1 mole of urea and about 1 mole of glyoxal with less than 2 moles of formaldehyde (about 1.4 to about 1.9 moles) in an aqueous medium at a pH between 6.2 and 6.7 at a temperature between 40° and 90° C. for a period of about 0.5 to 10 hours, reducing the pH of the reaction mixture in the second step by the addition of an acid to obtain a pH between 2.0 and 3.0 and maintaining a temperature between 40° and 90° C. for a period of at least about 0.5 to 3 hours, and in the third step adjusting the pH to between 5.0 and 7.0 by the addition of base thereto. The period for maintaining the temperature at a pH of 2 to 3 may be increased to more than 3 hours, but to no particular advantage. The free formaldehyde content of the product initially ranges from about 0.2% to about 1.0% on the weight of the solution but after several days it decreases to about 0.2% to 0.5%.

The reaction is preferably carried out in water and the formaldehyde used may be the commercial 37% or 44% formaldehyde solutions of paraformaldehyde.

In carrying out the process of the invention, certain features of the process of the invention are critical to obtaining successfully the improvements in the resulting product compositions. Thus, there are two critical features which are necessary, that is first, the reaction using a reduced amount of formaldehyde below the theoretical amount of 2 moles per mole of urea; and secondly, the maintenance of the temperature at about 40° to 90° C. at a pH of 2 to 3 for a period of at least 0.5 hours prior to adjusting the pH to between about 5.0 and 7.0 for carrying out the third step of the reaction.

Preferably in the first step of the process relative amounts of 1 mole of urea and 1 mole of glyoxal as a 40% aqueous solution are reacted with between 1.7 and 1.9 moles of formaldehyde as a 44% aqueous solution at a pH between 6.2 and 6.6 at a temperature between 55° and 65° C. until the amount of unreacted or free formaldehyde is about 0.5% to 1.0% by weight of the reaction mixture. It has been found convenient to maintain the temperature of the reaction mixture until the desired percentage of free formaldehyde is attained, the free formaldehyde content being determined by conventional analytical procedures. The pH can be conveniently maintained at 6.2 to 6.6 by the dropwise addition of 6.7% aqueous sodium bicarbonate as needed. When the first step of the process is finished the solution is normally cooled.

In the second step of the process the pH is preferably adjusted by the addition of an acidic material such as citric acid to a pH value between 2.4 and 3.0 and the temperature is raised to 60° C. and held between 55° and 65° C. for a period of at least 1.5 to 3.0 hours. The solution is then cooled to about 25° C. and in the third step of the process the pH of the final product is adjusted to a value between 5.0 and 7.0.

Examples of the acidic material useful for adjustment of the pH in the second step of the process to a pH of about 2 to 3 include: organic carboxylic acids such as citric, tartaric, gluconic, oxalic, malic, and the like; inorganic acids may also be used such as hydrochloric, nitric and the like although the use of carboxylic acids is generally preferred. A typical final product of this invention may be characterized as a composition containing 1,3-dimethylol-4,5-dihydroxy-2-imidazolidinone having between 1.6 and 1.9 moles of combined formaldehyde and from 0.02 to about 0.05 moles of free formaldehyde per mole of urea used plus water and about 5% of dissolved salts, depending on the acid used.

The typical product will be almost a water white liquid having a pH between 6.0 and 7.0. As stated above, the free formaldehyde should be less than 0.5% and preferably less than 0.2% on the weight of the product. The textile compositions obtained by the process of this invention are stable almost colorless solutions and are readily dilutable with water in all proportions.

The products of this invention are useful in imparting durable press properties to cellulosic textile materials and as such may be applied to such materials by any of the conventional procedures used in the textile industry. Thus, they may be applied by padding, dipping, spraying, immersing and the like. The products of this invention are superior to the durable press products of the prior art processes from the standpoint of the low levels of formaldehyde released from cellulosic materials prior to the conventional curing procedures. The low emission of formaldehyde after the drying operation and prior to the final curing step is an important improvement in post-cure durable pressing processing. The product of this invention may be employed with other textile agents and auxiliaries such as surface active agents, softeners, brighteners, odorants and other crease-proofing agents.

The nonionic surface active agent used in the examples is the condensation product of nonylphenol with an average of 9.5 moles of ethylene oxide. Other suitable nonionic surfactants can also be used, such as other alkyl aryl polyethylene glycol ethers and ethylene oxide adducts of straight chain alcohols.

In order to illustrate the present invention the following examples are given primarily by way of illustration but are not to be construed as limitative. All parts and percentages are by weight unless otherwise specifically designated.

EXAMPLE 1

To a suitable reaction vessel equipped with a stirrer and pH electrodes there is added 79.65 parts (1.165 moles) of 44% formalin, 8.85 parts of water, and 93.5 parts (0.65 mole) of 40% aqueous glyoxal. Sufficient sodium bicarbonate, about 8 parts of 6.8% aqueous sodium bicarbonate, is added while stirring to provide a pH of 6.2–6.6, followed by 39.0 parts (0.65 mole) of urea. The temperature of the reaction is raised to 50° C. and the temperature is allowed to rise to about 60° C. and is maintained at this level for 3¾ hours. During the 3¾ hour period, additional amounts of sodium bicarbonate are added as 6.8% aqueous sodium bicarbonate in order to maintain the pH at 6.2–6.6. Thus a total of 28 parts of 6.8% sodium bicarbonate is added during the 3¾ hour period.

The reaction mixture is cooled to about 40° C. and 8.9 parts of anhydrous citric acid is added to provide a pH of 2.7. The temperature is then raised to 60°±2°C. The reaction mixture is then stirred at pH 2.7 for 3 hours at 60° C. and the pH is then adjusted to 6.2–6.6 by the addition of 50% aqueous hydroxide. The reaction mixture is then diluted with water to give a total weight of 270 parts.

The product is an aqueous solution of 1,3dimethylol-4,5-dihydroxy-2-imidazolidinone containing about 45% solids and 0.7% of unreacted formaldehyde. After storage at room temperature for several days the solution contains 0.3% of unreacted formaldehyde.

EXAMPLE 2

Comparison of Formaldehyde Release

Two equeous pad baths were prepared the first containing 30% aqueous solution of 1,3-dimethylol-4,5-dihydroxy-2-imidazolidinone prepared by the process of the invention and the second by a modification of the formaldehyde ratio and holding time to represent the prior art. Applications were made by a conventional procedure to a 65/35 blend of polyester cotton (poplin fabric) with a 70% expression using 6% zinc nitrate as accelerator and 0.1% nonionic as surfactant (Decerosol NI) dried to about 5% moisture.

Using a standard formaldehyde release test (AATCC 112-1972, Levi Strauss Modification) the formaldehyde release in ppm of fabric was determined in each instance. The results are shown in the following table:

|  | Formaldehyde Release ppm of fabric (Avg. of 2 observations) |
| --- | --- |
| Product of Example 1 | 1127 |
| Product of process using a 2.0 to 1.0 ratio of formaldehyde to urea, no holding time (prior art) | 1342 |

EXAMPLE 3

Two aqueous pad baths (C & D) were prepared each both containing 25% of aqueous solution of 1,3-dimethylol-4,5-dihydroxy-2-imidazolidinone prepared by the process of this invention and modifications (A & B) of the formaldehyde ratios and holding times to represent the prior art as shown in Table 1.

Table I

| Pad Bath | Process Used | | Formaldehyde Release (ppm) (duplicates) | |
| --- | --- | --- | --- | --- |
|  | Mole HCHO/urea | 2.7 pH holding (hrs.) | | |
| A | 2.0/1.0 | 3.0 | 1520 | 3197 |
| B | 1.8/1.0 | 0 | 1559 | 1584 |

Table I-continued

| Pad Bath | Process Used Mole HCHO/urea | 2.7 pH holding (hrs.) | Formaldehyde Release (ppm) (duplicates) | |
|---|---|---|---|---|
| C | 1.8/1.0 | 1.5 | 1103 | 913 |
| D | 1.8/1.0 | 3.0 | 931 | 1014 |

The pad baths were applied by standard padding procedure to 65/35 polyester-cotton shirting fabric obtaining a 70% wet pick-up. The fabrics, containing about 30% on the weight of the fabric of aqueous solution of 1,3-dimethylol-4,5-dihydroxy-2-imidazolidinone were dried 1.5 minutes at 225° F. and analyzed for ppm formaldehyde release on the weight of the fabric. The results shown in Table I demonstrate that a combination of a lower-formaldehyde/urea mole ration and holding the mixture at a low pH for a period of time is necessary to produce a composition which greatly reduces the ppm of formaldehyde released from the fabrics treated therewith.

EXAMPLE 4

Pad baths were prepared, (A) containing an aqueous solution of 1,3-dimethylol-4,52-imidazolidine prepared by the process of the invention and (B) a prior art product described below. Applications were then made by conventional procedures to 65/35 polyester cotton shirting and the durable press result was noted using a standard AATCC test as well as the yellowing to scorch test, AATCC test.

In addition, for evaluation of forma,denyde release effects, the composition were applied by conventional procedures to polyester-cotton poplin; and to 1.34 cotton twill. Evaluation for formaldehyde release was then made according to method AATCC 112-1972, Levi Strauss modification.

Bath Composition: 25% reactant; 5% accelerator; 0.1% surfactant at pH 4.3

Bath A

Product of the Invention, similar to Example 1. Formaldehyde/glyoxal ratiio of 1.8 to 1; held 3 hours at 60° C. at a pH at 60 C.

Bath B

Prior art product, formaldehyde/glyoxal ratio of 2 to 1, no holding time.

Table II

Application to 65/35 Polyester Cotton Shirting

| | (25% reactant) Durable Press Appearance | |
|---|---|---|
| | 1 Wash | 2 Washes |
| Bath A (Process of the Invention) | 2.8 | 3.1 |
| Bath B | 3.1 | 3.1 |

Table III

| | Yellowing to Scorch 400° F. Initial | | | After Chlorine | | |
|---|---|---|---|---|---|---|
| | 30" | 60" | 90" | 30" | 60" | 90" |
| Bath A (Process of the Invention) | 4.75 | 4.50 | 4.00 | 4.75 | 4.50 | 4.00 |
| Bath B | 4.75 | 4.50 | 4.00 | 4.75 | 4.50 | 4.00 |

Table IV

| | Formaldehyde Release Test (25% reactant) Formaldehyde, ppm of fabric (Avg. of two observations) | |
|---|---|---|
| | Polyester/Cotton poplin | 1.34 Cotton twill |
| Bath A (Process of the Invention) | 396 | 502 |
| Bath B | 801 | 1,000 | used to prepare the reactant in that there is a substantial decrease in release of formaldehyde with the new product but at the same time the durable press and yellowing to scorch properties are retained.

I claim:

1. A process for producing a curable low formaldehyde releasing finish on cellulosic textile materials comprising:
    applying an aqueous solution of water-soluble urea-formaldehyde-glyoxal condensation product, an accelerator and a surface active agent to a cellulosic textile,
    drying the treated textile, and
    pressing the dried textile at elevated temperature;
    said water-soluble urea-formaldehyde-glyoxal condensation product prepared by a process comprising
    reacting in an equeous medium about 1.0 mole of urea, about 1.0 mole of glyoxal and less then 2.0 moles of formaldehyde at a pH maintained between 6.2 and 6.7 and at a temperature of 40° C. until the formation of 1,3-demethylol-4,5-dihydroxy-2-imidazolidinone is essentially completed,
    adding an acidic material to the reaction solution to adjust the pH between 2.0 and 3.0,
    maintaining the pH between 2.0 and 3.0 and at a temperature between 40° and 90° C. for a period of at least 0.5 to 3.0 hours and
    adding a base to the solution to adjust the final pH of the solution between 5.0 and 7.0.

2. A process according to the claim 1 wherein the cellulosic textile is treated with a single aqueous solution of the water-soluble urea-formaldehyde-glyoxal condensation product and the accelerator is zinc nitrate.

3. A process according to claim 2 wherein the surface active agent is a non-ionic material.

4. A process according to claim 3 wherein the amount of the water-soluble urea-formaldehyde-glyoxal condensation product applied to the cellulosic textile are in the range of 1 % and 15 % based on the weight of the fabric, the amount of zinc nitrate is between 5.5% and 16.5% based on the weight of the condensation product, the drying temperature is between 175° and 250° F and the pressing and curing temperature is between 300° and 420° F.

5. A process according to claim 4 wherein the amount of water-soluble urea-formaldehyde-glyoxal condensation product and surface active agent is in the range of from 3.0% and 8.9% and between 0.075% and 1% respectively, based on the weight of the fabric, the amount of zinc nitrate employed is between 09.5% and 12.5% based on the weight of the condensation product, the drying temperature is between 200° and 225° F., and the curing temperature is between 320° and 380° F.

6. A cellulosic textile material as obtained by the process of claim 1.

* * * * *